US006414143B1

(12) United States Patent
Cannizzo et al.

(10) Patent No.: US 6,414,143 B1
(45) Date of Patent: Jul. 2, 2002

(54) EXTRACTION AND RECOVERY OF NITRAMINES FROM PROPELLANTS, EXPLOSIVES, AND PYROTECHNICS

(75) Inventors: Louis Cannizzo, North Ogden; Lew Huntsmann, Willard, both of UT (US)

(73) Assignee: Alliant Techsystems Inc., Edina, MN (US)

( * ) Notice: Subject to any disclaimer, the term of this patent is extended or adjusted under 35 U.S.C. 154(b) by 0 days.

(21) Appl. No.: 09/505,872

(22) Filed: Feb. 17, 2000

Related U.S. Application Data

(60) Provisional application No. 60/121,493, filed on Feb. 24, 1999.

(51) Int. Cl.[7] .................... C07D 255/02; C07D 257/02; C07D 259/00; C07D 267/02; A62D 3/00

(52) U.S. Cl. ....................... 540/475; 149/124; 540/552; 540/554; 544/180; 588/203

(58) Field of Search ................... 588/203, 92; 149/124, 149/109.6; 540/475, 552, 554; 544/180

(56) References Cited

U.S. PATENT DOCUMENTS

| | | | | |
|---|---|---|---|---|
| 4,098,627 A | | 7/1978 | Tompa et al. | |
| 4,231,822 A | | 11/1980 | Roth | |
| 4,389,265 A | | 6/1983 | Tompa et al. | |
| 4,713,232 A | | 12/1987 | Chin et al. | |
| 5,011,614 A | | 4/1991 | Gresser et al. | |
| 5,221,486 A | | 6/1993 | Fassbender | |
| 5,284,995 A | | 2/1994 | Melvin | |
| 6,011,193 A | * | 1/2000 | Myler et al. | 588/203 |
| 6,013,794 A | * | 1/2000 | Nuquist | 540/475 |
| 6,063,960 A | | 5/2000 | Phillips et al. | |

OTHER PUBLICATIONS

Urbanski, T.; Chemistry and Technology of Explosives, vol. III, (1967) pp. 79, 117 (No month).

Leake, E.E. "Recovery of HMX From Scrap PBX–9404 High Explosive", Technical Report No. 219, AEC Operations Division, Oct. 26, 1973.

* cited by examiner

*Primary Examiner*—Wayne Langel
(74) *Attorney, Agent, or Firm*—Sullivan Law Group

(57) ABSTRACT

Nitramine oxidizers are recovered from propellant, explosive, and pyrotechnic materials with a concentrated mineral acid bath, preferably comprising 70 to 90 wt. % nitric acid, that serves to dissolve the nitramine oxidizers into solution and permit filtration of the binder therefrom. The recovery process is conducted in the absence of organic solvents.

20 Claims, No Drawings

EXTRACTION AND RECOVERY OF NITRAMINES FROM PROPELLANTS, EXPLOSIVES, AND PYROTECHNICS

RELATED APPLICATION

Priority is claimed of provisional application Ser. No. 60/121,493 filed in the U.S. Patent & Trademark Office on Feb. 24, 1999, the complete disclosure of which is incorporated herein by reference.

BACKGROUND OF THE INVENTION

1. Field of the Invention

This invention relates to the extraction and recovery of nitramine oxidizers from energetic materials, especially solid propellants, explosives, and pyrotechnics, and more particularly to an extraction and recovery process that is performed in the absence of organic solvent.

2. Description of the Related Art

Demilitarization has created a need for the economical and environmentally friendly non-hazardous disposal of solid explosives and propellants commonly found in rockets and ballistic missiles. An example of a propellant that is commonly found in rocket motors and missiles subject to demilitarization is Class 1.1 solid propellants. Generally, Class 1.1 solid propellants contain combinations of polymeric binders, plasticizers such as nitrate ester plasticizers, ballistic additives, chemical stabilizers, curing agents and catalysts, metal powders, and inorganic and/or organic oxidizers.

One class of organic oxidizer that has found wide acceptance in the rocket propulsion, explosive, and pyrotechnic arts comprises nitramine oxidizers. Common nitramine oxidizers include, for example, cyclotetramethylenetetranitramine (also known as HMX and 1,3,5,7-tetranitro-1,3,5,7-tetraaza-cyclooctane), cyclotrimethylenetrinitramine (also known as RDX and 1,3,5-trinitro-1,3,5-triaza-cyclohexane), and combinations thereof, as well as TEX (4,10-dinitro-2,6,8,12-tetraoxa-4,10-diazatetracyclo-[$5.5.0.0^{5,9}0^{3,11}$]-dodecane), and HNIW (also known as CL-20) (2,4,6,8,10,12-hexanitro-2,4,6,8,10,12-hexaazatetracyclo [$5.5.0.0^{5,9}0^{3,11}$]-dodecane). These nitramines are commonly among the most expensive and highly explosive ingredients of conventional energetic compositions, making their successful and efficient recovery for subsequent re-use highly desirable.

A method for the extraction and recovery of nitramine oxidizers from solid propellants is disclosed in U.S. Pat. No. 5,284,995 to Melvin, which discloses the use of a liquid ammonia extraction agent for extracting HMX and RDX from rocket motor solid propellants. The use of liquid ammonia in nitramine recovery techniques introduces several complexities and expenses, especially in a closed system, including high capital expenditures required as outlay to obtain equipment capable of operating at the high-pressures (5 to 40 Kpsi) at which liquid ammonia is handled. The presence of liquid ammonia also creates other problems, such as worker safety issues, since contact between the ammonia and human skin can cause severe chemical burns to the handler. Additionally, liquid ammonia is combustible, and presents a severe inhalation hazard if not handled correctly. Another disadvantage of the process of U.S. Pat. No. 5,284,995 is that subjecting energetic materials, such as Class 1.1 propellants containing nitramine oxidizers, to pressurized environments as described in the '995 patent increases the risk of accidental detonation, as well as the accompanying catastrophic consequences that an accidental detonation or explosion often has on human life and property.

Techniques for decomposing pyrotechnic materials with a combination of organic solvents and mineral acids are disclosed in U.S. Pat. No. 4,098,627 to Tompa et al. Representative mineral acids include hydrochloric acid, sulfuric acid, phosphoric acid, nitric acid and perchloric acid, which function to decompose cross-linked or linked polymeric binders present in the pyrotechnic materials. The organic solvent functions either to swell the organic polymeric binder present in the pyrotechnic material or to dissolve filler material present in the pyrotechnic material. Organic solvents reportedly suitable in the process are toluene, xylene, dioxane, and tetrahydrofuran. The decomposition technique is carried out at 80° to 120° C. In practice, however, these organic solvents raise a host of safety concerns, including flammability, VOC emissions, environmentally sound and cost-effective waste disposal, and handling expenses.

Two additional approaches for dissolution of pyrotechnic materials having polymeric binders are disclosed in U.S. Pat. No. 4,389,265 to Tompa et al. The first approach utilizes a solution of 2-aminoethanol in a mixture of an aromatic solvent and an alcohol. The second approach is performed with a solution of a mineral acid, other than nitric acid, water, and an organic solvent. The 2-aminoethanol employed in the first approach and the combination of mineral acid and organic solvent employed in latter approach serve to breakdown or dissolve the polymeric binder. Examples of aromatic solvents for the first approach include benzene, toluene, xylene, ethylbenzene, and diethylbenzene. Examples of organic solvents used in the second approach include acetone, methylethylketone, tetrahydrofuran, and mixtures thereof. Hydrochloric, sulfuric or phosphoric acid in concentrations from 2N to 6N are combined with one or more of the above-listed organic solvents. The presence of these aromatic and organic solvents raises safety concerns over such issues as flammability, volatile emissions, and waste disposal.

There is therefore a long-felt need in the art to develop a method for the recovery of nitramine oxidizers from energetic materials such as solid propellants, explosives, and pyrotechnics (hereinafter collectively referred to as "PEP formulations" or "PEP materials") in which there is no need for the use of either liquid ammonia under increased pressure or hazardous organic solvents that are volatile and/or flammable.

SUMMARY OF THE INVENTION

An object of this invention is to provide a nitramine-recovery method that addresses the above-described long-felt need in the art, is inexpensive and efficient, does not require the use of organic solvents as processing agents, and is suitable for the recovery of reusable nitramine oxidizers from PEP formulations, especially solid propellants of rocket motors such as ballistic missiles.

In accordance with the principles of this invention, the above and other objects are attained by the provision of a process in which nitramine oxidizers are extracted from PEP formulations with concentrated aqueous mineral acids, especially at least 70 wt. % nitric acid, in the absence of an organic solvent.

In accordance with one embodiment of this invention, the PEP formulation is treated in an acid bath comprising the concentrated aqueous mineral acid heated to a temperature sufficiently high to obtain a nitramine-containing solution. The solution is then filtered to generate a liquid filtrate containing the dissolved nitramine oxidizer. The filtrate is then diluted with a diluent such as water and/or treated with an acid-neutralizing agents such as aqueous sodium bicarbonate or sodium hydroxide or ammonia gas, which will cause the nitramine to precipitate out. The filtration of the nitramine-containing solution is performed at a temperature sufficiently high to keep the nitramine dissolved in the nitric acid solution. The nitramine oxidizer is then precipitated and isolated, for example, by filtering, drying, and washing the precipitate to yield the desired reusable nitramine oxidizer.

Suitable mineral acids for use in the aqueous concentrated mineral acid bath include, for example, hydrochloric acid, sulfuric acid, phosphoric acid, nitric acid, perchloric acid, and combinations thereof. Nitric acid is preferred as the mineral acid because of the high solubility of nitramines in nitric acid, especially nitric acid in a concentration of from about 70 to about 98 wt. %, preferably nitric acid at a concentration of up to 90 wt. % is utilized.

In accordance with a specific embodiment of this invention, in which the PEP formulation comprises a nitrate ester plasticizer, the process can also further comprise pretreating the PEP formulation with a hydrolysis agent to hydrolyze the nitrate ester prior to addition of the PEP formulation to the heated acid bath.

The nitramine oxidizer is recovered in yields typically on the order of 60 wt. % or higher based on the amount of oxidizer present in the PEP formulation.

These and other objects, features, and advantages of the present invention will become apparent from the following detailed description of the principles of this invention.

DETAILED DESCRIPTION OF THE INVENTION

Among the PEP formulations suitable for treatment by the present method are solid rocket motor propellants. The extraction method finds applicability to a wide array of binder systems for such solid propellants, including composite propellants, double-base propellants, crosslinked double-base propellants, and other plasticized propellants. Additionally, the present extraction method can be applied to PEP formulations in the form of explosive materials, such as plastic bonded explosives (PBX), melt cast explosives, and slurried explosives. Although the inventive process is meant to apply to most, if not all, PEP formulations, generally it can be uneconomical to apply the present method to PEP formulations containing less than about 10 wt. % nitramine.

PEP formulations containing nitrate ester compounds can be subjected to a hydrolysis pre-treatment stage prior to combining the PEP formulations with the concentrated aqueous mineral acid bath. Practice of the hydrolysis pretreatment stage is preferred for PEP formulations containing nitrate esters, such as nitrate ester plasticizers. Suitable hydrolysis agents for this pre-treatment stage include, by way of example, aqueous ammonia, dilute aqueous sodium hydroxide, dilute aqueous potassium hydroxide, dilute aqueous sodium sulfide, and dilute mineral acids, such as nitric acid, sulfuric acid, hydrochloric acid, perchloric acid, and the like. The hydrolysis agent should be sufficiently dilute so that decomposition of the nitramine oxidizers does not occur during or subsequent to the pre-treatment stage. Where this pre-treatment stage is practiced, the hydrolysis agent is preferably heated aqueous ammonia, which is effective in hydrolyzing nitrate esters found in PEP formulations. Suitable conditions for hydrolyzing most nitrate esters include 10% aqueous ammonia heated from about 60° C. to about 90° C. The hydrolyzed propellant can then undergo extraction with the concentrated aqueous mineral acid, preferably aqueous nitric acid, in the same manner as other PEP formulations. The presence of residual aqueous ammonia in the hydrolyzed propellant typically does not deleteriously affect the nitramine extraction.

Another optional, yet preferred, pre-treatment stage comprises reducing the size of the PEP material prior to its combination with the concentrated aqueous mineral acid bath. Preferably, the PEP material is solid and sized on the order of about 0.25 inch (0.64 cm) diameter or less. Conventional size reducing processes can be utilized, such as cutting or grinding in the presence of water.

Extraction of the nitramine oxidizer from the PEP formulation is performed in a concentrated aqueous mineral acid bath, with the mineral acid preferably being about 70 wt. % to about 98 wt. % aqueous nitric acid, most preferably being about 70 wt. % to about 90 wt. %, to dissolve the nitramine, but not the binder, into solution. During extraction, the bath is heated and can be agitated, with extraction lasting for several hours. Although a suitable duration time for the extraction and heating stages varies based on selected process conditions, determination of suitable duration periods can be accomplished without undue experimentation by controlling such conditions as the concentration of the acid, temperature of the extraction process, ratio of acid-to-oxidizer, size of the particles of PEP formulation, nature of the oxidizer, and the nature of the PEP binder. Due to the gradual decomposition of many nitramines in the presence of hot, concentrated aqueous nitric acid, the extraction process is optimally performed with either higher temperature and shorter times (less than several hours) or lower temperatures and longer times (more than several hours) to reduce, and preferably avoid, decomposition reactions. Generally, temperatures below the boiling point for the specific nitric acid solution are preferred.

The solution containing the dissolved nitramine oxidizer is then filtered to remove the non-dissolved binder and provide a filtrate containing the dissolved nitramine oxidizer. The filtrate is treated to induce the nitramine to precipitate, such as by dilution in water. The precipitated nitramine oxidizer can then be recovered and purified. Filtration can be performed using suitable liquid/solid separation techniques, such as, for example, filter press or centrifugal separation.

During the extraction process, nitric oxides ($NO_x$) can be generated in significant quantities. The nitric oxides generated during the extraction process can be removed from the extraction vessel by conventional means, such as, for example, a $NO_x$ scrubber.

In accordance with another embodiment of this invention, the extraction process can be conducted in a continuous manner. In this continuous extraction process, a highly concentrated nitric acid solution (of about 90 wt. % or higher nitric acid) is pumped into and through a vessel containing the PEP material from which nitramines are to be extracted. Preferably the PEP material is composed of very finely ground particles with an average size of less than about 0.1 inch (0.25 cm) in diameter. The nitric acid solution can be pumped through the PEP material numerous times to extract the nitramines. Preferably the extraction process is done at ambient temperature or less than about 30° C. Following extraction of the nitramines from the PEP material, water is added to the nitric acid solution to precipitate the nitramines, which are further treated as set forth above.

The following examples serve to explain embodiments of the present invention in more detail. These examples are not to be construed as being exhaustive or exclusive as to the scope of this invention.

EXAMPLES

Example 1

A 125 ml Erlenmeyer flask equipped with septum, needle, stir bar, and thermometer was charged with 36 ml of 70 wt. % $HNO_3$. The nitric acid was stirred and heated to 50° C. Over the next six hours a total of 5.0 grams of an aluminized propellant containing about 10 to about 20 wt. % HMX was added in small portions to the heated aqueous nitric acid. The propellant was broken into small pieces less than 0.25 inch (0.64 cm) in diameter, prior to addition. One hour after completion of addition of the propellant, stirring was stopped, and the mixture filtered hot through a coarse frit. The filtrate was diluted with water to 200 ml and allowed to stand overnight. Precipitate was filtered off and dried to give a 81% yield of HMX.

Example 2

The same procedure as used in Example 1 was followed, except that the acid bath was heated to 70° C., a total of 5.004 grams of aluminumized propellant were added over 2 hours, and the mixture was stirred and heated for one hour after the addition of the propellant was complete. Total yield of 63% of recovered HMX.

Example 3

A double base propellant comprising nitrate esters was pre-treated with hot aqueous ammonia, to destroy the nitrate esters. The resulting powdery residue comprised approximately 25 wt. % HMX, aluminum powder, hydrated alumina, and decomposed binder.

Following the same procedure set forth in Example 1, a total of 2.00 grams of the powdery residue having an average particle size of less than 100 microns was added, except all of the residue was added at once.

The mixture was then stirred and heated at 50° C. for 3 hours. The mixture was filtered hot through a coarse frit. The filtrate was diluted to 200 ml with water and allowed to stand overnight. Precipitate was filtered off and dried to give a total yield of 66% of HMX.

Example 4

A 125 ml Erlenmeyer flask equipped with septum, needle, stir bar, and thermometer was charged with 36 ml of concentrated, 70 wt. %, $HNO_3$. The nitric acid was stirred and heated to 50° C. and 2.000 grams of a PBX explosive, cut into 0.25 inch pieces containing 80–90 wt. % RDX, were added portion-wise over the next hour and a quarter to the acid bath. No change in temperature of the acid bath was observed upon initial addition of the propellant. Upon completion of addition of the propellant, the mixture was heated for an additional 15 minutes, and filtered hot through a coarse frit. The filtrate was diluted with water to 200 ml and allowed to stand overnight. The precipitate was filtered off and dried to give a total yield of 68% of recovered RDX.

Example 5

A 125 ml Erlenmeyer flask equipped with septum, needle, stir bar, and thermometer was charged with 36 ml of concentrated, 70 wt. %, $HNO_3$. The nitric acid was heated to 70° C. and 2.0036 grams of a PBX explosive comprising 80–90 wt. % RDX were added portion-wise over the next hour to the acid bath. No change in temperature of the acid bath was observed upon initial addition of the propellant. After all of the propellant was added to the bath, the mixture was heated for another 1.5 hours and then filtered hot through a coarse frit. The filtrate was diluted with water to 200 ml and allowed to stand overnight. The precipitate was filtered off and dried to give a total yield of 70% of recovered RDX.

The foregoing detailed description of the preferred embodiments of the invention has been provided for the purpose of explaining the principles of the invention and its practical application, thereby enabling others skilled in the art to understand the invention for various embodiments and with various modifications as are suited to the particular use contemplated. This description is not intended to be exhaustive or to limit the invention to the precise embodiments disclosed. Modifications and equivalents will be apparent to practitioners skilled in this art and are encompassed within the spirit and scope of the appended claims.

What is claimed is:

1. A process for extracting nitramine oxidizers from nitramine-containing energetic materials selected from the group consisting of propellants, explosives, and pyrotechnics, and recovering the nitramine oxidizers, said process comprising:

combining an energetic material comprising one or more nitramine oxidizers and one or more binders with an acid bath comprising a concentrated inorganic acid, the acid bath having a sufficiently high concentration of concentrated inorganic acid and being heated to a sufficiently high temperature to dissolve the nitramine oxidizers into solution, the solution being free of organic solvent;

filtering the solution to remove the binders and provide a filtrate containing the nitramine oxidizers; and precipitating the nitramine oxidizer from the filtrate and isolating the nitramine oxidizer.

2. A process according to claim 1, wherein said precipitating of the nitramine oxidizer comprises diluting the filtrate with and precipitating the nitramine oxidizer in at least water.

3. A process according to claim 1, further comprising grinding or cutting the energetic material into relatively small particles prior to said combining of the energetic material with the binders.

4. A process according to claim 1, wherein the concentrated inorganic acid is at least one member selected from the group consisting of hydrochloric acid, sulfuric acid, phosphoric acid, nitric acid, and perchloric acid.

5. A process according to claim 1, wherein the concentrated inorganic acid comprises nitric acid.

6. A process according to claim 5, wherein the acid bath comprises from about 70 wt. % to about 98 wt. % nitric acid.

7. A process according to claim 1, wherein the energetic material comprises at least one nitrate ester compound, and wherein said process further comprises pre-treating the energetic material with at least one hydrolysis agent to hydrolyze the nitrate ester compound prior to said combining.

8. A process according to claim 7, wherein the hydrolysis agent comprises at least one member selected from the group consisting of aqueous ammonia, dilute aqueous sodium hydroxide, dilute aqueous potassium hydroxide, dilute aqueous sodium sulfide, and dilute mineral acid.

9. A process according to claim 7, wherein the concentrated inorganic acid is at least one member selected from the group consisting of hydrochloric acid, sulfuric acid, phosphoric acid, nitric acid, and perchloric acid.

10. A process according to claim 7, wherein the concentrated inorganic acid comprises nitric acid.

11. A process according to claim 10, wherein the acid bath comprises from about 70 wt. % to about 98 wt. % nitric acid.

12. A process for extracting nitramine oxidizers from nitramine-containing energetic materials selected from the group consisting of propellants, explosives, and pyrotechnics, and recovering the nitramine oxidizers, said process comprising:

combining an energetic material comprising one or more nitramine oxidizers and one or more binders with an aqueous bath comprising nitric acid, the aqueous bath having a sufficiently high concentration of nitric acid and being heated to a sufficiently high temperature to dissolve the nitramine oxidizers into solution, the solution being free of organic solvent;

filtering the solution to remove the binders and provide a filtrate containing the nitramine oxidizers; and precipitating the nitramine oxidizer from the filtrate and isolating the nitramine oxidizer.

13. A process according to claim 12, wherein said precipitating of the nitramine oxidizer comprises diluting the filtrate with and precipitating the nitramine oxidizer in at least water.

14. A process according to claim 12, wherein the aqueous bath comprises from about 70 wt. % to about 98 wt. % nitric acid.

15. A process according to claim 12, further comprising grinding or cutting the energetic material into relatively small particles prior to said combining of the energetic material with the binders.

16. A continuous process for extracting nitramine oxidizers from nitramine-containing energetic materials selected from the group consisting of propellants, explosives, and pyrotechnics, and recovering the nitramine oxidizers, said process comprising:

combining in a continuous processing vessel an energetic material comprising one or more nitramine oxidizers and one or more binders with an aqueous bath comprising nitric acid;

heating the aqueous bath and recirculating the aqueous bath through the continuous processing vessel for a sufficient time to dissolve the nitramine oxidizers into solution, the solution being free of organic solvent;

filtering the solution to remove the binders and provide a filtrate containing the nitramine oxidizers; and precipitating the nitramine oxidizer from the filtrate and isolating the nitramine oxidizer.

17. A process according to claim 16, wherein said precipitating of the nitramine oxidizer comprises diluting the filtrate with and precipitating the nitramine oxidizer in at least water.

18. A process according to claim 16, wherein the energetic material comprises at least one nitrate ester compound, and wherein said process further comprises pre-treating the energetic material with at least one hydrolysis agent to hydrolyze the nitrate ester compound prior to said combining.

19. A process according to claim 16, further comprising grinding or cutting the energetic material into relatively small particles prior to said combining of the energetic material with the binders.

20. A process according to claim 16, wherein aqueous bath comprises greater than 90 wt. % nitric acid.

* * * * *